United States Patent [19]

Ferenczy et al.

[11] Patent Number: 4,729,951
[45] Date of Patent: Mar. 8, 1988

[54] PROCESS FOR THE IMPROVEMENT OF ANTIBIOTIC PRODUCTION BY IN VIVO GENETIC RECOMBINATION

[75] Inventors: Lajos Ferenczy; Antal Mai, both of Szeged; István Ott, Budapest; Gábor Ambrus, Budapest; Tibor Láng, Budapest, all of Hungary

[73] Assignee: Biogal Gyogyszergyar, Debrecen, Hungary

[21] Appl. No.: 610,774

[22] Filed: May 16, 1984

[30] Foreign Application Priority Data

May 16, 1983 [HU] Hungary .............................. 1678/83

[51] Int. Cl.$^4$ ....................... C12P 19/48; C12N 15/00; C12N 1/20; C12R 1/465
[52] U.S. Cl. .................................. 435/80; 435/172.2; 435/253; 435/886; 935/90
[58] Field of Search ...................... 435/172.2, 80, 253, 435/886; 935/90

[56] References Cited

U.S. PATENT DOCUMENTS 4,159,226  6/1979  Baltz ..................................... 935/90

FOREIGN PATENT DOCUMENTS 1602074  11/1981  United Kingdom ............. 435/172.2

OTHER PUBLICATIONS

Ochi, K. *Journal of Bacteriology*, 150 (2): 592–597, 1982.
Hopwood, D. A. *Ann. Rev Microbiol* 35: 237–72, 1981.

Primary Examiner—Thomas G. Wiseman
Assistant Examiner—Karen Maurey
Attorney, Agent, or Firm—Keil & Weinkauf

[57] ABSTRACT

A process for the production of aminoglycoside antibiotics using fused protoplasts derived from streptomyces. The cells are precultured in a medium containing sucrose, calcium and magnesium salts. Protoplasts are formed and then fused. The fused protoplasts are regenerate and antibiotic producing ability is screened for. The regenerate cells produced an antibiotic complex of modified composition or demonstrated increased or reduced antibiotic productivity compared to the fusion partners.

14 Claims, No Drawings

PROCESS FOR THE IMPROVEMENT OF ANTIBIOTIC PRODUCTION BY IN VIVO GENETIC RECOMBINATION

The invention relates to a process for the improvement, both qualitative and quantitative, of antibiotic production in microorganisms, by means of in vivo genetic recombination.

More particularly, the invention relates to a process for the production of fermentation broth containing aminoglycoside antibiotics by cultivating such genetically modified Streptomycetes with modified antibiotic producing abilities, obtained by the in vivo genetic recombination.

Aminoglycoside antibiotics are widely used drugs of major therapeutic and commercial importance. Due to their broad antibacterial potency they are used both in human and in veterinary practice.

It is known that *Streptomyces tenebrarius* synthesizes nebramycin, a multicomponent mixture of antibiotics [Stark, Hoehn and Know: Antimicrobial Agents and Chemotherapy 1967, 314, British Pat. No. 1,178,489, U.S. Pat. No. 3,691,279 and Hungarian Pat. No. 176,103]. Umezawa et al produced kanamycin with *Streptomyces kanamyceticus* ATCC 12853 [J. Antibiotics, 10A, 181 (1957) and Japan Kokai No. 8695 (1961)]. The kanamycin components A, B and C are also aminoglycoside antibiotics.

It is also known that the cells of microorganisms of the Streptomycetaceae family (Streptomyces and Micromonospora strains) can be converted under suitable conditions into protoplasts (cell-wall-free form), and subsequently they can be again regenerated into normal cells (Okanishi, Suzuki and Umezawa: J. Gen. Microbio. 80, 389 (1973), U.S. Pat. No. 4,294,927).

The fusion of protoplasts from different strains induces genetic recombination, furnishing cells which contain modified genetic information [i.e. Hopwood, Wright and Bibb: Nature 268, 171 (1977); Alföldi, Szvoboda et al; U.S. Pat. No. 4,294,927 (1978); Godfrey, Ford and Huber: Canadian J. Microbiol. 24, 994 (1978); Oichi, Hitchcock and Katz: J. Bact. 139, 984 (1979)]. These experiments were performed with amino acid-, nucleotide base- or vitamin-deficient auxotrophic strains. The genetic recombination itself was confirmed for example by the fusion of protoplasts, prepared from cells with a requirement for uracil, with protoplasts with a requirement for cystein, and after regeneration, isolating prototrophs non-deficient in these requirements (Oichi et al, see former citation).

Baltz et al in Belgian Pat. Nos. 868,472 and 868,473 specified a process for the preparation and regeneration of Streptomyces protoplasts as well as for fusion of protoplast from auxotrophic cells but failed to report any results as regards the effects of recombination on antibiotic biosynthesis.

To our knowledge the improvement of aminoglycoside antibiotic production by in vivo genetic recombination by protoplast fusion has not yet been reported in the literature.

It was the objective of the present invention to develop a process whereby antibiotic biosynthesis could be influenced both qualitatively and quantitatively, by in vivo genetic recombination, wherein the quality and the quantity of the biologically active compounds, synthesized by antibiotic producer microorganisms, could be altered advantageously.

Unexpectedly, it was found that the antibiotic synthesizing ability of a certain portion of recombinant cells, prepared by protoplast fusion according to the process of the invention, was modified in surprisingly large proportion compared to the total number of recombinant strains. Some of the recombinants produced an antibiotic complex of modified composition, while the productivity of others became either highly increased or reduced compared to that of the fusion partners.

Furthermore, it was found that the efficacy of both protoplast fusion, and even more that of regeneration, could be significantly increased by the process of the invention.

Furthermore it was unexpectedly found that we were able to isolate recombinants after crosses of some genetically marked and nongrowing protoplasts inactivated by chemical or physical agents.

Accordingly the present invention provides a process for the production of fermentation broths containing aminoglycoside antibiotics from Streptomycetes modified in antibiotic producing ability by in vivo genetic recombination. The process comprises the preparation of protoplasts, after precultivation in the presence of sucrose and calcium and magnesium salts, from the cells of genetically marked and one or more prototrophic or unmarked Streptomycetes, and making fusions, using either two strains bearing genetic markers, or using one genetically marked strain and one or more prototrophic or unmarked strains inactivated either by chemical or physical methods, regenerating the fused protoplasts, isolating the resulting strains having modified genetic material, determining the antibiotic producing capacity of the cells having modified genetic material, selecting the strains with preferably modified antibiotic producing ability, and carrying out aerated, submerged fermentations with the novel strains obtained in a medium containing organic carbon and nitrogen sources, inorganic salts, trace elements, and/or oils of animal or plant origin, and/or fats.

According to a preferred method of the invention amino acid- or nucleotide base-deficient auxotrophic strains were prepared. In some experiments auxotrophs were produced by mutagenic treatment with N-methyl-N'-nitro-N-nitrosoguanidine [Davis, J. Am. Chem. Soc., 70, 4267 (1948)]. The antibiotic-producing ability and genetic stability of the resulting auxotrophs was screened. The genetically stable isolates were cultivated in liquid medium containing organic carbon and nitrogen sources, sucrose, calcium and magnesium ions, and glycine (the glycine inhibits cell growth). The culture, where glycine inhibition was strongest though not complete, was selected, the cells were centrifuged and washed. The washed cells were suspended in isoosmotic solution containing sucrose and lysozyme, and protoplasts were formed. The protoplast suspension obtained was washed and one portion of it was plated on solid regenerating agar containing organic carbon and nitrogen sources, sucrose, calcium and magnesium ions, and agar. The other portion of protoplasts was combined in an 1:1 ratio with protoplasts prepared in a similar manner from partner cells selected for genetic recombination. Polyethyleneglycol (m.w. 1000 to 20,000) and salts dissociating to magnesium and calcium ions were added to the protoplast mixture which induced the fusion of protoplasts. Subsequently the cells were regenerated. Only hybrid cells which actually underwent in vivo genetic recombination were able to form colonies if regeneration was carried out in minimal medium. However, regeneration can also be performed in a medium containing organic nitrogen source. Then the prototroph count can be determined if the colonies grown in this medium are replicated into minimal medium.

In the course of the above procedure prototrophic recombinants were isolated after the fusion of protoplasts prepared from one or several auxotrophic strains. However, the conversion of some of the antibiotic-producer strains into auxotrophs strongly lowered their productivity. Considering industrial interests it looked advantageous if at least one of the fusion partners selected was biosynthesizing large amounts of antibiotics. So a process was developed where only a single auxotrophic strain was used, while the other partner in the fusion was a prototrophic strain in which the protoplasts were made non-viable by either chemical or physical treatment prior to fusion. After fusion ony the recombinant prototrophs were regenerated or developed colonies, while the auxotrophs or killed prototrophs were unable to regenerate or grow.

The inactivation of protoplasts was performed either by chemical or physical methods. Any chemical agent ensuring the loss of regenerating ability, while preserving the genetic integrity of protoplasts, can be used, e.g. cannabidiolic acid (3-methyl-6-isopropenyl-4'-n-pentyl-2',6-dihydroxy-1,2,3,6-tetrahydrodiphenyl-3'-carboxylic acid) and its salts, N-ethylmaleimide, pyrrolnitrin [3-chloro-4-(3-chloro-2-nitrophenyl)-pyrrole], brilliant green (N-[4-{[4-(diethylamino)phenyl]-phenylmethylene}-2,5-cyclohexadien-1-ylidene]-N-ethylethanaminium sulfate and 2-mercaptoethanol. After the chemical inactivation the protoplasts were washed and fusion was carried out.

According to the process of the invention the protoplasts can also be inactivated by gamma-irradiation. Protoplasts were irradiated by a $^{60}$Co isotope at doses of 30 to 120 krad, preferably 80 krad, the protoplasts were centrifuged and used as fusion partners.

The antibiotic-producing ability of the resulting prototrophic isolates was screened. After fusion the productivity of double auxotrophs and of the prototrophs obtained from them by segregation was also determined.

The productivity of the strains was screened by inoculating media preferably containing organic carbon and nitrogen sources, inorganic salts and vegetable oils, and incubating the cultures. After 16 to 24 hours these seed cultures were used to inoculate the main fermentation medium, having the same composition as the seed medium, and fermentation was continued for 140 to 160 hours. Sampling was started in the 96th hour and was repeated in every 24th hour. The antibiotic content and the component ratio of the antibiotics produced were assayed.

The recombinants prepared by the above procedure, and found to be good antibiotic producers, were cultivated in submerged, aerated conditions in a medium containing organic carbon and nitrogen sources, inorganic salts, oils of plant and/or animal origin, and/or fats, at 25° to 40° C., preferably at 28° to 37° C., till the accumulation of suitable amounts of the antibiotic.

Recombinants can be prepared from *Streptomyces tenebrarius* MNG 169 and MNG 204 strains, deposited at the National Collection of Microorganisms of the National Institute for Public Health, Budapest. *Streptomyces tenebrarius* MNG 169 (deposited on Dec. 28, 1977) can synthesize nebramycin-2, nebramycin-4 and nebramycin-5', while *Streptomyces tenebrarius* MNG 204 (deposited on Sept. 2, 1981) can produce nebramycin-5' and trace amounts of nebramycin-4. From these strains auxotrophic mutants were prepared by the usual mutagenic treatment with N-methyl-N'-nitro-N-nitroso-guanidine. The genetic stability of these mutants was controlled after several passages, and their antibiotic synthesizing ability was screened. The genetically stable strains were selected, and protoplasts were formed according to the procedure described in the Examples. The protoplasts were combined with the corresponding fusion partner and regeneration was carried out. Both protoplast formation and regeneration were found to proceed with a yield of nearly 100 percent if cultivation, protoplast formation and regeneration were carried out in the presence of sucrose and salts dissociating to calcium and magnesium ions (for example calcium or magnesium chloride, sulfate or nitrate). The regenerated prototrophic recombinants were isolated and cultivated on agar slants. The frequency of prototroph formation from auxotrophic strains, which amounted only to $10^{-8}$ in the case of spontaneous mutations, amounted to $1\times10^{-3}$ to $5\times10^{-4}$ in the fusion process of the invention.

On studying the productivity of the isolated prototrophic recombinants it has been found that the individual antibiotics present in the antibiotic complex, produced by the parent strains, were also produced by each recombinant but in a changed component ratio and at altered production levels. The parent strains MNG 204 produced two and, respectively, three (MNG 169) nebramycin components, while the self-fusion of the protoplasts of the strains MNG 204 and MNG 169 or the fusion of the protoplasts of strains MNG 204 and MNG 169 furnished genetic recombinants which either a. failed to produce any antibiotic, or produced very low or very high antibiotic levels compared to the parent strains, or produced b. a single nebramycin component: nebramycin-2, nebramycin-4 or nebramycin-5', respectively;

c. two nebramycin components: nebramycin-2 and nebramycin-4, or nebramycin-2 and nebramycin-5', or nebramycin-4 and nebramycin-5'; or d. three nebramycin components: nebramycin-2, nebramycin-4 and nebramycin-5'.

From the strains obtained the nebramycin-2 producer *Streptomyces tenebrarius* 35TL was deposited under number MNG 00243, the nebramycin-4 producer *Streptomyces tenebrarius* F104 under number MNG 00244, while the nebramycin-5' producer *Streptomyces tenebrarius* F77 under accession number MNG 00242 on Nov. 25, 1982 at the National Collection of Microorganisms of the National Institute for Public Health, Budapest.

The strains of the invention can produce fermentation broths containing nebramycin components. The fermentation is preferably carried out according to the procedure of Hungarian Pat. No. 176,103, and the antibiotics are preferably isolated by the process of Hungarian Pat. Nos. 174,315 and 176,103.

According to a further preferred method of the invention the strain *Streptomyces kanamyceticus* can be applied for producing recombinants. The cultivation of the microorganism, the preparation of protoplasts, their fusion and regeneration, furthermore the screening of the productivity of the selected strains are carried out as described above or according to the procedure described in Examples 3 and 8.

The process of the invention provides multiple advantages. The diploidization or recombination ensuing at its application can effect the biosynthesis of antibiotic(s) in the strains either by advantageously changing the component ratio or by producing higher antibiotic levels.

The following examples are illustrating but not limiting the scope of invention.

EXAMPLE 1

Preparation of protoplasts, protoplast fusion and regeneration

Agar slants were inoculated with the spore suspension of *Streptomyces tenebrarius* MNG 169 and MNG 204 or with auxotrophic strains prepared from them. Composition of the agar slant used:

| Dextrin | 1.0% |
|---|---|
| Yeast extract | 0.1% |
| Casein hydrolysate (10%)+ | 2.0% |
| Meat extract | 0.1% |
| Cobalt dichloride hexahydrate | 0.001% |
| Agar | 2.5% |

+Hydrolyzed enzymatically.

Prior to sterilisation the pH of the medium was adjusted with an aqueous sodium hydroxide solution to 7.2, the medium was sterilized at 121° C. for 20 minutes.

The cultures were incubated at 37° C. for 4 days, then the spores were washed off the surface of the agar slant with sterile, distilled water. The spore suspension obtained was used to inoculate a sterile seed medium of the following composition:

| Glucose | 1.0% |
|---|---|
| Yeast extract | 1.0% |

The pH of the medium was adjusted to 7.2.

The cultures were incubated at 37° C. for 48 hours, then 0.2 ml of this seed medium was used to inoculate a sterile medium of the following composition:

| Glucose | 1.0% |
|---|---|
| Yeast extract | 1.0% |
| Sucrose | 20.5% |
| Calcium dichloride dihydrate | 0.3% |
| Magnesium dichloride hexahydrate | 0.6% |
| Glycine | 4.5 or 6% |

The pH of the medium was adjusted to 7.0–7.2.

The cultures were incubated on a rotary shaker at 37° C. for 48 hours, then the culture in which the growth inhibition of glycine was strong though not complete was selected. This culture was utilized to repeatedly inoculate the above glycine containing media, but the glycine concentrations were increased. I.e., if the selected culture contained originally 4 percent of glycine, reinoculation was carried out into media containing 5 and 6 percent of glycine.

The mycelium formed was separated by centrifuging for 15 minutes at 2300 g, then the mycelium was washed with a solution having the following composition:

| Sucrose | 20.5% |
|---|---|
| Calcium dichloride dihydrate | 0.3% |
| Magnesium dichloride hexahydrate | 0.6% |
| Potassium chloride | 0.0075% | pH of the solution: 7.2, designation: M. The mycelium was subsequently centrifuged.

Following centrifuging the mycelial mass was resuspended in the above solution and 0.5 percent of lysozyme was added to the suspension (Serva, Feinbiochemie, Heidelberg). The mycelium was incubated with gentle shaking, and the protoplast formation was monitored microscopically every 10 minutes. Depending on the strain species, complete protoplast formation of the mycelial Streptomyces culture usually required an incubation period of 1 to 4 hours.

The culture, transformed completely (100%) into protoplasts, was centrifuged (2300 g, 25 minutes), washed with solution M, then was repeatedly centrifuged.

The sediment was cautiously suspended in 0.05 ml of solution M, then the protoplasts were regenerated.

For the removal of any remaining mycelium the protoplast suspension to be regenerated was filtered through a 2.5 cm deep layer of compact cotton fibres. The filtrate, diluted with solution M, was plated to a sterile regeneration agar with the following composition:

| Glucose | 1.0% |
|---|---|
| Yeast extract | 1.0% |
| Sucrose | 20.5% |
| Calcium dichloride dihydrate | 0.3% |
| Magnesium dichloride hexahydrate | 0.6% |
| Agar | 3.0% | pH of the solution: 7.0–7.2.

0.1 ml of the protoplast suspension was plated on the surface of 25 ml of regeneration agar as a basal layer in a Petri dish, then 3 ml of a regenerating agar cover was layered over it. The composition of the agar cover was identical to that of the basal layer agar except that it contained 1.2 percent of agar, instead of 3 percent.

The cultures were incubated at 35°–37° C. in a humid chamber. On the 3rd or 4th day the regenerating colonies were already freely visible. Compared to the protoplast count plated to the regenerating plate regeneration was practically quantitative.

Where the fusion of protoplasts involved two auxotrophs, the following minimal medium was used for plating if only the regeneration of prototrophic recombinants was required from the hybrids present:

| Diammonium sulfate | 0.5% |
|---|---|
| Potassium dihydrogen phosphate | 0.1% |
| Magnesium sulfate heptahydrate | 0.05% |
| Glucose | 1.0% |
| Calcium chloride dihydrate | 0.3% |
| Magnesium chloride hexahydrate | 0.6% |
| Sucrose | 20.5% |
| Wickerham vitamin solution | 0.01% |
| Agar | 3.0% | pH of the medium: 7.2.

Composition of the Wickerham vitamin solution:

| | |
|---|---|
| Folic acid | 0.2 mg |
| Biotin | 0.2 mg |
| Calcium pantothenate | 40.0 mg |
| Inositol | 200.0 mg |
| Niacin | 40.0 mg |
| p-Amino-benzoic acid | 20.0 mg |
| Pyridoxin hydrochloride | 40.0 mg |
| Aneurine hydrochloride | 40.0 mg |
| Riboflavin | 20.0 mg |
| Distilled water | 100.0 ml |

Prototrophs could also be isolated by replicating the colonies, grown in complete regeneration medium, on a minimal medium of the above or of other composition.

According to an advantageous process of the invention protoplast fusion may be carried out according to the above method by mixing the protoplasts, prepared from two or more strains, at any desired or preferably 1:1 ratio, then adding to 0.2 ml of this protoplast mixture 2 ml of the fusion solution having the following composition:

| | |
|---|---|
| Polyethylene-glycol, m.w.: 4000 | 35.0% |
| Calcium dichloride dihydrate | 0.3% |
| Magnesium dichloride hexahydrate | 0.6% |

The pH of the solution was adjusted to 7.2 with aqueous sodium hydroxide solution.

On the addition of the fusion solution the protoplasts aggregated and their membranes fused. After fusion was complete, the DNA-s of two or several cells, bearers of genetic information, were brought into adjacent positions, enabling the realisation of genetic recombination.

Table 1 presents the efficacy of protoplast formation and regeneration carried out with the process of the invention and with the known process of the Belgian Pat. Nos. 868,472 and 868,473.

TABLE 1

Formation and regeneration of protoplasts from *Streptomyces tenebrarius* by known processes and by the process of the invention

| Method | Protoplast formation % (90 min) | Regeneration Colony count | % | Colonies formed from intact cells Colony count | % |
|---|---|---|---|---|---|
| Known | 92.5 | 13 | 0.065 | 1500 | 7.5 |
| Present invention | 99.81 | 18000 | 90.0 | 38 | 0.19 |

The Table clearly demonstrates that the efficacy of protoplast formation and especially that of regeneration can be substantially increased with the process of the invention by preliminary cultivation in the presence of calcium chloride, magnesium chloride and sucrose.

In the following examples some in vivo genetic recombination experiments and their results are presented.

EXAMPLE 2

Fusion of auxotrophic strains and the antibiotic biosynthesis of recombinant strains a. Fusion of auxotrophic A222 his⁻ and 404ura⁻ strains The histidine deficient A222 his⁻ and uracil deficient 404 ura⁻ strains, obtained by usual mutagenic treatment, were prepared from *Streptomyces tenebrarius* MNG 204, producing nebramycin-5' and traces of nebramycin-4, and from *Streptomyces tenebrarius* MNG 169, synthesising nebramycin-2, nebramycin-4 and mebramycin-5'.

Protoplasts were formed from the two strains according to the procedure described in Example 1, and the protoplasts were submitted to fusion and regeneration. A portion of the prototrophic recominants was isolated. The recombination frequency amounted to $5 \times 10^{-5}$.

The antibiotic-producing capability of the isolated prototrophs was assayed according to the procedure described in Example 8. The results of fermentations carried out with 147 isolated recombinants are presented in Table 2.

TABLE 2

Antibiotic production of prototrophs obtained by the in vivo DNA recombination of A222 his⁻ and 404 ura⁻ auxotrophic strains

| Production | No. of strains | % |
|---|---|---|
| No antibiotic production | 16 | 10.9 |
| Nebramycin-5' | 24 | 16.3 |
| Nebramycin-4 | 11 | 7.5 |
| Nebramycin-4 and -5' | 57 | 38.8 |
| Nebramycin-2 and -5' | 7 | 4.7 |
| Nebramycin-2, -4 and -5' | 32 | 21.8 |

Production capacity of partners participating in the fusion:

| | | |
|---|---|---|
| A222 his⁻: | nebramycin-2: | 0 μg/ml |
| | nebramycin-4: | 30 μg/ml |
| | nebramycin-5' | 675 μg/ml |
| 404 ura⁻: | nebramycin-2: | 1120 μg/ml |
| | nebramycin-4: | 75 μg/ml |
| | nebramycin-5': | 145 μg/ml |

The production capacity of some recombinants at the same time significantly surpasses that of the partners participating in the fusion. Thus *Streptomyces tenebrarius* F 105 synthesizes 2140 μg/ml of nebramycin-2, 380 μg/ml of nebramycin-4 and 1510 μg/ml of nebramycin-5'; *Streptomyces tenebrarius* F 88 produces 0 μg/ml of nebramycin-2, 140 μg/ml of nebramycin-4, and 1440 μg/ml of nebramycin-5'; and *Streptomyces tenebrarius* F 104 produces 1520 μg/ml of nebramycin-4 beside traces of nebramycin-5' (less than 1 percent).

The productivity of strains isolated after the self-fusion of protoplasts prepared from parent strains failed to exhibit any change.

Applying the process described in Example 8 10 liters of a fermentation broth were prepared with *Streptomyces tenebrarius* F 104. The compounds exhibiting biological potency were isolated according to the procedure described in Hungarian Pat. No. 174,315, yielding 13.8 g of nebramycin-5 (kanamycin-B) and 9 mg of nebramycin-6 (tobramycin).

*Streptomyces tenebrarius* F 77 and F 104 were deposited under numbers MNG 00242 and MNG 00244 at the National Collection of Microorganisms of the National Institute for Public Health, Budapest.

b. Fusion of auxotrphic 7-34 trp⁻ and 73 lys⁻ strains

Tryptophane-deficient *Streptomyces tenebrarius* 7-34 trp⁻ and lysine-deficient *Streptomyces tenebrarius* 73 lys⁻ strains were obtained from *Streptomyces tenebrarius* MNG 169 by usual mutagenic treatment. Protoplasts were formed from the two strains according to the process described in Example 1, and the protoplasts were fused and regenerated. Some of the prototrophs were isolated and their production capacity analyzed according to the procedure described in Example 8. The recombination frequency amounted to $1 \times 10^{-5}$.

TABLE 3

Antibiotic production of prototrophs obtained by the in vivo DNA recombination of 7-34 trp$^-$ and 73 lys$^-$ auxotrophic strains

| Production | No. of strains | % |
|---|---|---|
| No antibiotic production | 1 | 2.9 |
| Nebramycin-2 | 2 | 5.9 |
| Nebramycin-2 and -5' | 16 | 47.3 |
| Nebramycin-2, -4 and -5' | 15 | 43.9 |

Partners participating in the fusion snythesize all three nebramycin components.

Following fusion and regeneration it was found that some of the strains were unable to grow on minimal medium in the presence of lysine or tryptophane, while rapid growth was observed in the common presence of lysine and tryptophane. Due to the recombination the original auxotrophic strains became double auxotrophs (trp$^-$lys$^-$). The productivity of all three double auxotrophs was analyzed according to the procedure described in Example 8, and the results are presented in Table 4. Following segregation two prototrophs were isolated from the double auxotrophs, and their antibiotic production pattern is also shown.

TABLE 4

Antibiotic production of double auxotroph trp$^-$ lys$^-$ and of the segregants isolated from them

| Strain | Nebramycin component produced | % |
|---|---|---|
| Streptomyces tenebrarius trp$^-$ lys$^-$ | nebramycin-2 | 23.1 |
|  | nebramycin-2 and -4 | 7.7 |
|  | nebramycin-2 and -5' | 30.7 |
|  | nebramycin-2, -4 and -5' | 30.5 |
| Streptomyces tenebrarius prototroph 35 W and 40 W | nebramycin-4 and -5' | 100.0 |

As is apparent from the Table, the productivity of the strains isolated following in vivo genetic recombination was substantially altered. It is of special interest that the prototrophs, isolated from the double auxotrophs, have lost their ability to synthesize apramycin, but at the same time the amount of antibiotics produced was significantly higher than that produced by the original strains. Recombinants 7-34 trp$^-$ and 73 lys$^-$ produced 1300 to 1700 μg/ml of nebramycin-2, 200 μg/ml of nebramycin-4 and 1040 μg/ml of nebramycin-5', while recombinants 35 W and 40 W synthesized 1040 μg/ml of nebramycin-4 and 1950 μg/ml of nebramycin-5'.

Streptomyces tenebrarius 35 TL, producing solely nebramycin-2, was deposited under number MNG 00243 at the National Collection of Microorganisms of the National Institute for Public Health, Budapest.

c. Fusion of auxotrophic J1006-3ade$^-$ and J211/2ura$^-$ strains

Streptomyces tenebrarius J1006-3ade$^-$ and J211/2ura$^-$ were prepared from strain MNG 204 by mutagenic treatment. The strains either failed to produce antibiotics or produced only trace amounts of nebramycin-5' (less than 5 μg/ml). Following their fusion, carried out according to the procedure described in Example 1, the productivity of 150 prototrophic recombinants was investigated according to the method described in Example 8. The frequency of recombination amounted to $1 \times 10^{-4}$.

60 percent of the strains investigated (90 strains) retained their non-producer property, while 40 percent (60) synthetisized either nebramycin-4 and nebramycin-5', or solely nebramycin-5'. 13 percent (8) of the producer strains yielded more than 1500 μg/ml of antibiotic.

The results confirm that the antibiotic-producing ability of Streptomycetes can be significantly increased by the process of the invention.

EXAMPLE 3

Fusion of Streptomyces kanamyceticus leu$^-$ and arg$^-$ auxotrophic strains

The procedure described in Example 1 was used except that the cultivation of the strains with genetic markers was continued at 28° C. until growth in the medium containing 3 percent of glycine was detectable.

The auxotrophic strains were isolated from Streptomyces kanamyceticus ATCC 12 853 [(Umezawa et al.: J. Antibiotics 10A, 181 to 188, (1957) and Japan Kokai 8695 (1961)] following mutagenic treatment. The parent strain itself produced kanamycin. The leucine-deficient mutant failed to produce any antibiotic, while the mutant growing in the presence of arginine on minimal medium could synthesize 15 μg/ml of kanamycin.

The antibiotic production of Streptomyces kanamyceticus was monitored according to the method described in Example 8 except that cultivation was carried out at 28° C. instead of 37° C. and Bacillus subtilis was applied as test organism.

The prototrophs were isolated after fusion and regeneration of the fused protoplasts, and the productivity of 144 strains was analysed. 12 strains were able to synthesize a tenfold amount of kanamycin in relation to that produced by the arginine-deficient auxotroph (about 155 μg/ml). The frequency of recombination amounted to $3-8 \times 10^{-4}$.

EXAMPLE 4

Preparation of intact but non-viable protoplasts and their use as fusion partners Protoplasts were prepared from Streptomyces tenebrarius MNG 169 and the 404 ura$^-$ auxotrophic mutant of this strain according to the procedure used in Example 1. In order to inactivate the protoplasts derived from the prototrophic Streptomyces tenebrarius MNG 169 triethyl amine salt of cannabidiolic acid (3-methyl-6-isopropenyl-4'-n-pentyl-2',6'-dihidroxy-1,2,3,6-tetrahydro-diphenyl-3'-carboxylic acid) was added in 50–100 μg/ml concentration to the protoplast suspension ($10^8$ protoplast/ml of medium M). After 4 hours treatment at 30° C. the protoplasts were centrifuged (2300 g, 25 min) and washed with medium M, and centrifuged again in order to remove the residual part of the inactivating agent. The fusion of the chemically inactivated protoplasts of the prototrophic Streptomyces tenebrarius MNG 169 and the protoplasts of its 404 ura$^-$ mutant was carried out according to Example 1.

The results are presented in Table 5.

TABLE 5

| Strain | Regenerating plate Number of colonies/ml | Regenerating plate Treatment with cannabidiolic acid Number of colonies/ml | Minimal medium Number of colonies/ml | Recombination frequency |
| --- | --- | --- | --- | --- |
| MNG 169 | $2 \times 10^4$ | 0 | $2.1 \times 10^4$ | — |
| 404 ura$^-$ | $1.5 \times 10^4$ | — | 0 | — |
| MNG 169 × 404 ura$^-$ | — | — | 30 | $2 \times 10^{-3}$ |

EXAMPLE 5

Preparation of intact but non-viable protoplasts and their use as fusion partners Inactivated *Streptomyces tenebrarius* protoplasts were prepared in substantial accordance with the method of Example 4 except that 80–240 μg/ml pyrrolnitrin or 100–300 μg/ml of brilliant-green was used in place of cannabidiolic-acid triethylamine salt. The protoplasts were inactivated in 100%. The resulting non-viable protoplasts were used as fusion partners.

EXAMPLE 6

Preparation of intact but non-viable protoplasts and their use as fusion partners Protoplasts were prepared in substantial accordance with the method of Example 3, except that unmarked *Streptomyces kanamyceticus* was used in place of genetically marked one. From the resulting *Streptomyces kanamyceticus* ATCC 12853 protoplasts inactivated protoplasts were prepared in substantial accordance with the method of Example 4 except that N-ethylmaleimide (EM) rather than cannabidiolic-acid triethylamine salt was used. The results are presented in Table 6.

TABLE 6

| | Number of colonies on regenerating plate | | |
| --- | --- | --- | --- |
| Strain | Non-treated | Treated with 400 μg/ml EM | Treated with 800 μg/ml EM |
| *Str. kanamyceticus* | $3.2 \times 10^6$ | $4.2 \times 10^5$ | 0 |

The protoplasts treated with 800 μg/ml of N-ethylmaleimide were used as fusion partners.

EXAMPLE 7

Preparation of non-viable protoplasts by physical inactivation

The *Streptomyces tenebrarius* protoplasts, prepared according to Example 1 ($10^8$ cells/ml) were placed into a plastic tube and were irradiated by gamma-rays ($^{60}$Co). The inactivated cells, which received a dose of 80 krad, were used in crosses.

EXAMPLE 8

Productivity of strains synthesizing nebramycin antibiotic components and preparation of fermentation broths containing antibiotics The spores or the vegetative culture of the strain to be investigated was inoculated to an agar slant prepared with distilled water and having the following composition:

| | |
| --- | --- |
| Dextrin | 1.0% |
| Yeast extract | 0.1% |
| Casein hydrolysate (10%)$^+$ | 2.0% |
| Meat extract | 0.1% |
| Cobalt dichloride hexahydrate | 0.001% |

| | |
| --- | --- |
| Agar | 2.5% |

$^+$Hydrolyzed enzymatically.

The pH of the medium was adjusted prior to sterilisation to 7.2 with an aqueous sodium hydroxide solution, then sterilisation was carried out at 121° C. for 20 minuntes.

The cultures were incubated at 37° C. for 4 days, then the spores were washed off the surface of the medium with sterile distilled water, and the spore suspension obtained was used to inoculate two times 100 ml volumes of inoculum medium, prepared with tap water, sterilized in 500 ml Erlenmeyer flasks and having the following composition:

| | |
| --- | --- |
| Soy meal | 2.0% |
| Casein hydrolysate (10%)$^+$ | 3.0% |
| Ammonium nitrate | 0.1% |
| Ammonium chloride | 0.3% |
| Calcium carbonate | 0.3% |
| Magnesium sulfate heptahydrate | 0.5% |
| 1:1 mixture of palm oil and linseed oil | 3.0% |
| Glucose (sterilized separately as a 50 percent solution) | 2.0% |

$^+$hydrolyzed enzymatically

The pH of the medium was adjusted to 7.2 with an aqueous sodium hydroxide solution, then sterilisation was carried out in an autoclave at 121° C. for 20 minutes.

The inoculated cultures were cultivated at 37° C. for 14 to 18 hours on a rotary shaker (diameter 2.4 cm, 280 rpm).

This inoculum was used to inoculate the main fermentation medium which was either poured in 100 ml portions into 500 ml Erlenmeyer flasks and sterilized there, or in a 5 liter volume into a laboratory fermentor having a working volume of 10 liters and sterilized at 121° C. for 45 minutes. The main fermentation medium, prepared with tap water, had the following composition:

| | |
| --- | --- |
| Soy meal | 3.0% |
| Casein hydrolysate (10%)$^+$ | 5.0% |
| Ammonium nitrate | 0.1% |
| Ammonium chloride | 0.5% |
| L-glutaminic acid | 0.8% |
| Calcium carbonate | 0.5% |
| Magnesium sulfate heptahydrate | 0.5% |
| Cobalt dinitrate hexahydrate | 0.001% |
| 1:1 mixture of palm oil and linseed oil | 3.0% |
| Glucose (sterilized separately in 50 percent solution) | 4.2% |

$^+$hydrolyzed enzymatically

The pH of the medium was adjusted prior to sterilisation to 7.2 with aqueous ammonium hydroxide solution.

Cultivation was carried out at 37° C., the Erlenmeyer flasks were placed on the former rotary shaker, while the stirrer of the fermentor was operated at 360 rpm and a sterile air flow was passed through the medium at 3 liters per minute.

The antibiotic content of the culture was measured by agar-diffusion assay in the usual way and by bioautography, following thin-layer chromatography.

*Staphylococcus epidermidis* was applied as test organism in the routine agar-diffusion assays, while nebramycin-2- and nebramycin-4-resistant *Rhizobium meliloti* was utilized as test organism for the specific measurement of nebramycin-5'.

The antibiotic composition of the mixture was determined by thin-layer chromatography using silicagel (Merck, Darmstadt) as adsorbent and a 1:1:1 mixture of ethanol, methyl-ethyl ketone and 25 percent aqueous ammonium hydroxide as developing solvent. 0.1 to 0.5 µg/ml portions of the antibiotic solution were spotted to the plates. After drying a medium containing *Bacillus subtilis* ATCC 6633 was layered over the surface of the plate which was subsequently incubated at 37° C. for 16 hours. The size of the inhibition zones was measured compared to the standard. The assay is suitable for both quantitative and qualitative determination [J. Kádár Pauncz and J. Harsányi, J. Chromat. 195, 251 (1980)].

What we claim is:

1. A process for the production of fermentation broths containing aminoglycoside antibiotics from Streptomycetes modified in antibiotic-producing ability by in vivo genetic recombination which comprises preparing a cultivation medium consisting essentially of sucrose and calcium and magnesium salts;

cultivating genetically marked aminoglycoside antibiotic-producing Streptomycetes in said cultivation medium;

separately cultivating prototrophic or unmarked aminoglycoside antibiotic-producing Streptomycetes;

preparing protoplasts of said cultivated genetically marked Streptomycetes and of said cultivated prototrophic or unmarked Streptomycetes;

chemically or physically inactivating said prototrophic or unmarked Streptomycetes protoplasts to make them nonviable;

fusing said protoplasts of genetically marked Streptomycetes with said inactivated protoplasts of prototrophic or unmarked Streptomycetes;

regenerating the fused protoplasts;

assaying the resulting strains for antibiotic-producing capacity;

selecting the strains with enhanced antibiotic-producing ability; and carrying out aerated, submerged fermentations with the novel strains so obtained in a medium containing organic carbon and nitrogen sources, inorganic salts, trace elements, and oils or fats or mixtures thereof.

2. The process as claimed in claim 1, wherein protoplast formation, fusion and regeneration are carried out in a medium containing 0.1–0.5% of calcium salt, 0.3–0.8% of magnesium salt and 12–34% of sucrose.

3. The process of claim 2, wherein the chemical inactivation is performed with cannabidiolic acid and its salts, N-ethylmaleimide, pyrrolnitrin, brilliant green on 2-mercaptoethanol.

4. The process of claim 2, wherein the physical inactivation is performed with gamma-rays.

5. The process of claim 2, wherein the genetically marked Streptomyces strain is *Streptomyces tenebrarius*.

6. The process of claim 2, wherein the genetically marked Streptomyces strain is *Streptomyces kanamyceticus*.

7. The process of claim 1, wherein the chemical inactivation is performed with cannabidiolic acid and its salts, N-ethylmaleimide, pyrrolnitrin, brilliant green on 2-mercaptoethanol.

8. The process of claim 7, wherein the genetically marked Streptomyces strain is *Streptomyces tenebrarius*.

9. The process of claim 7, wherein the genetically marked Streptomyces strain is *Streptomyces kanamyceticus*.

10. The process of claim 1, wherein the physical inactivation is performed with gamma-rays.

11. The process of claim 10, wherein the genetically marked Streptomyces strain is Streptomyces tenebrarius.

12. The process of claim 10, wherein the genetically marked Streptomyces strain is *Streptomyces kanamyceticus*.

13. The process of claim 1, wherein the genetically marked Streptomyces strain is *Streptomyces tenebrarius*.

14. The process of claim 1, wherein the genetically marked Streptomyces strain is *Streptomyces kanamyceticus*.

* * * * *

UNITED STATES PATENT AND TRADEMARK OFFICE
CERTIFICATE OF CORRECTION

PATENT NO. : 4,729,951
DATED : March 8, 1988
INVENTOR(S) : Lajos FERENCZY et al.

It is certified that error appears in the above-identified patent and that said Letters Patent is hereby corrected as shown below:

Column 14, line 16

. . . . green[on]

should be:

. . . green or

Column 14, line 27

. . . . green[on]

should be:

. . . . green or

Signed and Sealed this

Twelfth Day of July, 1988

*Attest:*

DONALD J. QUIGG

*Attesting Officer*    *Commissioner of Patents and Trademarks*